United States Patent [19]
Sastri

[11] Patent Number: 5,630,826
[45] Date of Patent: May 20, 1997

[54] TUBULAR SURGICAL CUTTING INSTRUMENTS WITH COATING

[76] Inventor: Suri A. Sastri, 10 Bicentenial Dr., Lexington, Mass. 02173

[21] Appl. No.: 26,123

[22] Filed: Mar. 1, 1993

Related U.S. Application Data

[63] Continuation of Ser. No. 902,769, Jun. 23, 1992, abandoned, which is a continuation of Ser. No. 570,026, Aug. 20, 1990, abandoned.

[51] Int. Cl.$^6$ ................................................. A61B 17/32
[52] U.S. Cl. ........................................... 606/170; 606/180
[58] Field of Search ................................. 606/170, 167, 606/168, 180; 175/409

[56] References Cited

U.S. PATENT DOCUMENTS

| | | | |
|---|---|---|---|
| 3,990,751 | 11/1976 | Murdoch | 308/8.2 |
| 4,054,426 | 10/1977 | White | 51/309 |
| 4,190,301 | 2/1980 | Lachonius et al. | 308/8.2 |
| 4,304,444 | 12/1981 | Persson | 308/8.2 |
| 4,627,882 | 12/1986 | Söderström | 148/14 |
| 4,745,035 | 5/1988 | Saurer et al. | 428/614 |
| 4,762,189 | 8/1988 | Tatum | 175/371 |
| 4,923,441 | 5/1990 | Shuler | 606/170 X |
| 4,958,621 | 9/1990 | Topel et al. | 128/4 |

*Primary Examiner*—Danton D. DeMille

[57] ABSTRACT

A surgical instrument for use in endoscopic surgical procedures and especially arthroscopic surgery having an outer elongated tubular member and a concentric inner elongated tubular member positioned in and rotatable within the outer tubular member having an opening in its distal end and the inner tubular member having a cutting edge positioned at its distal end so as to coincide with and be exposable through the opening in the outer tubular member to effect the cutting of tissue and the removal of the cut tissue by aspiration through the inner tubular member, a coating of a metal from the group consisting of silver and gold extending substantially around the circumferential surface of at least one of the outer surface of the inner tubular member or the inner surface of the outer tubular member, the metallic coating from the group consisting of silver and gold being of such thickness and extending a sufficient distance along the axial length of the member to which it is applied to provide a malleable surface which more precisely controls and facilitates the rotation of the inner tubular member within the outer tubular member so as to virtually eliminate the production of metallic wear debris which can make its way to the incision site resulting in undesirable contamination and which can also reduce the scoring of the walls that can lead to the seizure of the surgical tool.

19 Claims, 1 Drawing Sheet

TUBULAR SURGICAL CUTTING INSTRUMENTS WITH COATING

This is a continuation of application Ser. No. 07/902,769 filed on Jun. 23, 1992 now abandoned which is a continuation of application Ser. No. 07/570,026 filed on Aug. 20, 1990 now abandoned.

FIELD OF INVENTION

The present invention relates to surgical instruments for use in endoscopic surgical procedures and especially arthroscopic surgery in which the instrument comprises an inner tubular member which has a cutting edge disposed on the distal end and which is rotatable in an outer tubular member having an opening at its distal end which opening is positioned so as to expose the cutting edge and to co-operate with the cutting edge in severing tissue and removing it by aspiration through the inner tubular member.

BACKGROUND OF THE INVENTION

Presently, endoscopic procedures such as arthroscopic surgery, in which a minimum of cutting is done to obtain access to the diseased or injured tissue, are widely employed. Generally, by keeping the amount of cutting to a minimum, the recuperation time may be substantially reduced. In such procedures, access to the problematical area is achieved through small incisions which are just large enough to permit the insertion of a fiber optic bundle connected to a T.V. camera for viewing the procedure, a tube for bathing the area with saline solution and an elongated tubular cutting instrument for cutting the tissue in question and removing the tissue by aspiration through the inner channel of the instrument. Generally such tubular cutting instruments comprise an inner tubular member which is positioned in and rotatable in an outer, concentric, elongated, tubular member at speeds of about 1000 to 3500 revolutions per minute. The elongated concentric tubes are usually about three to ten inches in length and the diameter of the outside tube is usually less than about 0.25 inch. The inner tubular member has a cutting edge disposed at its distal end which coincides with a corresponding opening in the distal end of the outer tubular member which (opening) provides the cutting edge with access to the tissue to be excised and co-operates with the cutting edge in carrying out the excision. The severed tissue is removed by bathing the area with a saline solution which is removed by aspiration through the inner tubular member. In order to provide aspiration and rotation, the proximal end of the inner tubular member is fixedly attached in the axial bore of a shaft member, usually molded from plastic which is provided with (1) a lateral bore for connecting the axial bore to an aspiratory chamber which can be positioned around the shaft and (2) coupling means for connecting the shaft to an electric motor which provides the rotational drive. In turn, the proximal end of the outer tubular member is fixedly attached in the axial bore of a handle member, also usually molded from plastic, in which the axial bore thereof opens into an enlarged axial cylindrical chamber for receiving and facilitating the rotation of the shaft to which the inner tubular member is joined. In order for the surgeon to position the cutting edge precisely at a particular site, the inner tubular member and the outer tubular member should have the least space between them commensurate with the ability for the inner tube to freely rotate at high speeds. Usually, a clearance of 0.0005 inch to 0.001 inch is provided. Typically the tubes are produced in a deep drawing process from sheet material of stainless steels such as those from the 300-series. Commercially produced tubes typically are not perfectly uniform with regard to concentricity, straightness and surface roughness. The manufacturers of arthroscopic surgical instruments have tried to compensate for such defects by procedures such as centerless grinding, precision straightening and honing and lapping of the tubular surfaces as well as application of lubricants such as silicones. Such procedures improve the performance in the early phases of the operation of the surgical instrument. However, after a few seconds of operation, problems related to metal-on-metal wear begin to occur thus hampering the smooth operation of the instrument. The rubbing of one stainless steel surface against another results in the production of metallic wear debris which can deposit in the incision site resulting in metal contamination, possible damage to the tissue and slow recovery or even failure of the procedure. Another problem with the production of these stainless steel particles is that they in turn cause further wear and scoring of the rotating surfaces that may lead to seizure and failure of the instrument. The current invention is concerned with overcoming such problems and providing improved tubular cutting instruments.

SUMMARY OF THE INVENTION

In the present invention, it has been found that the shearing off of metallic particles which creates undesirable wear debris and the possible seizure of the instrument can be virtually eliminated by applying a circumferential surface coating of a soft and malleable metal from the group consisting of silver and gold along at least a portion of the working length of at least one of the outer surfaces of the inner tubular member or the inner surface of the outer tubular member. This coating provides on such members a malleable surface with excellent resistance to wear which allows more precise control and virtually contamination-free operation of the instrument by the surgeon. It has been found that such a coating of metal from the group consisting of silver and gold also reduces the generation of hot spots, significantly lessens the need for using lubricants such as silicones and allows the cutting instrument to be operated at higher revolutions per minute.

One object of the present invention is to provide improved tubular surgical cutting instruments in which a circumferential surface coating of a metal from the group consisting of silver and gold is present along at least a portion of the working length of at least one of the outer surface of the inner tubular member or the inner surface of the outer tubular member.

Another object of the present invention is to provide improved tubular surgical instruments as set forth above in which said circumferential surface coating of the metal from the group consisting of silver and gold is present along at least a portion of the working length of the outer surface of the inner tubular member.

Still another object of the present invention is to provide improved tubular surgical instruments as set forth above in which said circumferential surface coating of the metal from the group consisting of silver and gold is present along at least a portion of the working length of the inner surface of the outer tubular member.

A further object of the present invention is to provide improved tubular surgical instruments as set forth above in which said circumferenti of the metal from the group consisting of silver and gold are present on adjacent areas on the outer surface of the inner tubular member and the inner surface of the outer tubular member.

Other objects of the invention should be clear from the following detailed description taken together with the drawings.

PRIOR ART

Donald K. Schuler U.S. Pat. No. 4,923,441, issued May 8, 1990, describes ways of bringing about improvements in such tubular cutting instruments which prevent cocking and skewing of the inner tubular member relative to the outer tubular member and which also prevent galling. Such improvements are brought about by applying a hard coating of titanium nitride by physical vapor deposition techniques along the entire outer surface of the inner tubular member to provide a hard bearing surface extending from the distal end to the proximal end.

Although such improvements address the cocking, skewing, galling and seizure problems, they do not address the problem of the shearing off of metallic stainless steel particles from the inner surface of the outer tubular member which (particles) can make their way into the incision site and adversely contaminate it and also lead to seizure of the instrument. As to this shearing problem, it appears that the hard coating of titanium nitride may actually exacerbate the tendency of metallic particles to be sheared off from the sorer, less tough stainless steel inner walls of the outer tubular member. In the present application, the improvements are brought about by going in the opposite direction from said U.S. Pat. No. 4,923,441; namely by applying a soft, malleable coating of a metal from the group consisting of silver and gold which not only resolves the galling and seizure problem but also virtually eliminates the shearing off of metallic stainless steel particles from the tubular members which is far more critical from a medical standpoint.

Silver and gold have been routinely used as coatings on dinnerware, cutlery and the like. Such use has been mainly for aesthetic reasons and the mechanical properties which make such metals useful in the present invention do not come in to play. Accordingly, such use of silver and gold on dinnerware and cutlery does not teach or suggest their usefulness on the tubular cutting instruments of the present invention, or the unexpected results obtained from such use.

On pages 802 to 822 of Volume III of the Metals Handbook, 9$^{th}$ Edition, 1980, there is a discussion of sliding bearings and the metals and ceramics which can be used in such bearings. In the second column on page 805, it is disclosed that silver and gold meet the theoretical criteria of compatibility with steel because of their favorable atomic size differences relative to iron and that such compatibility is a characteristic of anti-seizing and anti-scoring materials. As to gold, there are no further discussion of its other physical properties nor is there any mention of any instances where it is used as a bearing material. Absent such disclosures of its other physical properties and end uses, there is nothing in this reference to suggest gold's usefulness in the tubular cutting instrument of this invention and especially in its unexpectedly virtually eliminating the shearing problems in such instruments. As to silver, its use as a bearing material is further discussed at length on page 818 wherein it is pointed out that silver possesses poor surface characteristics and it is invariably used as an intermediate layer with an outer layer of another bearing material in heavy duty applications. Nowhere in this reference was there found an example in which silver was used as the primary bearing surface as the applicant has employed it in his tubular surgical instruments and unexpectedly found that it not only solved the galling and seizure problems but also solved the more critical problem of the shearing off of metallic particles. In using silver as a primary bearing surface, the present invention goes in the opposite direction from the teachings of the Metals Handbook reference, as was the case with U.S. Pat. No. 4,923,441 to bring out the unexpected improvements.

DETAILED DESCRIPTION OF THE INVENTION

Figure 1:
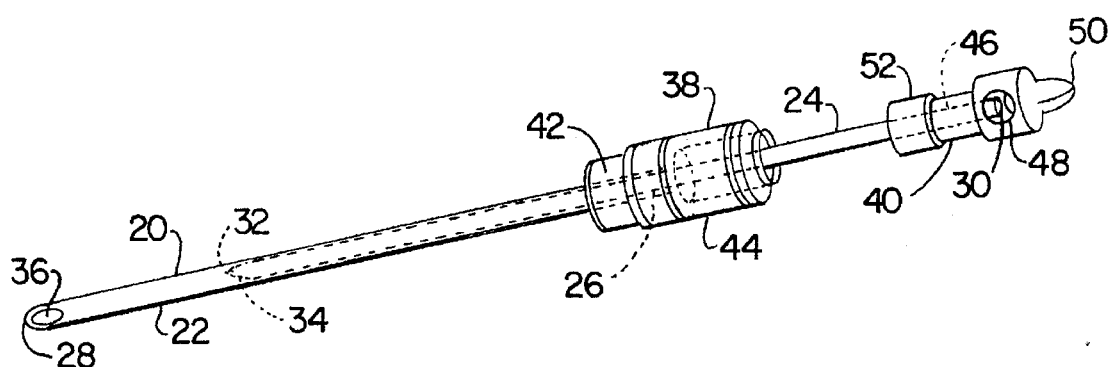
FIG. 1 is a perspective view of a tubular surgical instrument of the invention in which the inner tubular member is only partially inserted into the outer tubular member.
Figures 2, 3:
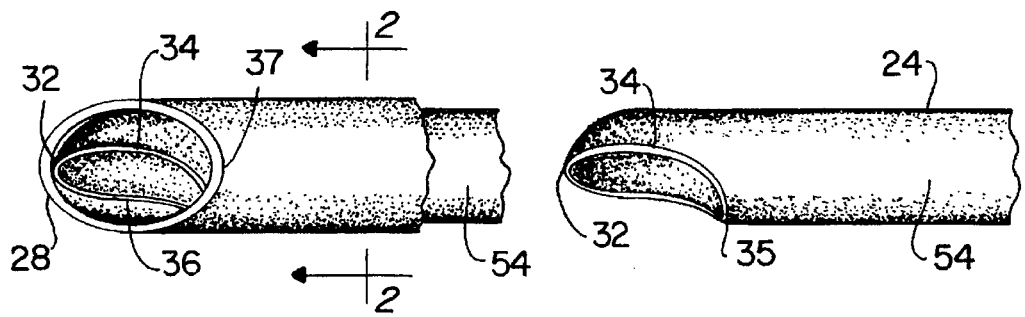
FIG. 2 is an enlarged perspective view of the distal end of tubular surgical cutting instruments within the scope of the present invention.
FIG. 3 is an enlarged perspective view of the distal end of an inner tubular member of a tubular surgical instrument within the scope of the present invention.

In FIG. 1, there is shown a tubular surgical cutting instrument 20 within the scope of this invention which is made up of an outer tubular member 22 usually formed of the 300-series austenetic stainless steel and an inner tubular member 24 also usually formed of the same stainless steel which is shown partly inserted into outer tubular member 22. Inner tubular member 24, which is fully insertable and rotatable in the outer tubular member 22, has, on the distal end 32, a cutting edge 34 which lies adjacent to the opening 36 in the distal end 28 of an outer tubular member 22 when inner tubular member 24 is fully inserted within outer tubular member 22 (FIG. 2). The cutting edge 34 may have the geometry and configuration of any of the many types of edges which are used for the various cutting, abrading, burring, etc. steps in such surgical procedures. The proximal end 26 of outer tubular member 22 is fixedly attached in the axial bore 42 of handle member 38 which is usually formed of plastic and the proximal end 30 of inner tubular member 24 is fixedly attached within the axial bore 46 of shaft member 40 which is also usually formed from plastic. The axial bore 42 in handle 38 opens into an enlarged cylindrical chamber 44 which serves as a female bearing for receiving and facilitating the rotation of male bearing 52 of shaft member 40 when inner tubular member 24 is fully inserted into outer tubular member 22. The proximal end 30 of inner tubular member 24 extends into a lateral channel 48 which provides access to an aspiration chamber (not shown) which can be positioned around the shaft member 40 for carrying out aspiration. A tang 50 is provided on the proximal end of the shaft member 40 for use in coupling to an electric motor (not shown).

The coatings of metal from the group consisting of silver and gold which extend substantially around the circumference of the tubular members can be readily applied by well-known electroplating processes from aqueous solutions. The coatings may also be applied by the equally well-known vapor deposition processes involving for example evaporation, sputtering or ion-plating. Especially good performance is obtained in the case of gold when a vacuum vapor deposition process is used in applying the coating. The coating thickness, which can be easily controlled in the coating processes chosen, may usually be varied provided it comes within the tolerances which are desired for rotating the inner tubular member 24 within the outer tubular member 22. Generally, the thickness of the coatings will be between about 60 Angstroms (approximately 0.25 millionths of an inch) to about 25 microns (approximately one thousandths of an inch). The preferred thickness of the coating metal from the group consisting of silver and gold will be between 0.12 microns to 1.5 microns (5 to 60 millionths of an inch).

It has been found desirable also to coat the tubular members with sub-coats of metals such as chromium and nickel or ceramics such as carbides and nitrides of zirconium, titanium, hafnium, tantalum, niobium, vanadium, tungsten and silicon and mixtures thereof before applying the coating of the metal from the group consisting of silver and gold. Also, in embodiments in which the soft metal coating is applied to only one tubular member, such metal and ceramic coatings may be applied along at least a portion of the working length of the other tubular member with beneficial results. For purposes of this invention, the term "working length" when used in reference to the inner tubular member 24 refers to the length of said inner tubular member 24 from the distal end 32 to the point at which it is attached to the distal end of the shaft member 40 and when used in referenceto the outer tubular member 22 refers to the length of said outer tubular member 22 from the distal end 28 to the point at which it is attached to distal end of the handle-member 38. Such metal and ceramic coatings may be applied along at least a portion of the working length of the tubular members by known sputtering and ion-plating processes and, in the case of chromium and nickel coatings, they can also be applied by known vapor deposition processes and by electroplating. Usually the thicknesses of such metal and ceramic coatings may be varied within the tolerances required for rotation but generally thicknesses of about 10 to 200 millionths of an inch will provide the beneficial results.

For best results it is usually desirable to smooth and polish the surfaces of the stainless steel tubular members which are to be used in forming the surgical instrument in the present invention. Especially desirable results have been obtained by smoothing such surfaces using electropolishing techniques which are well known in the art. Generally the electropolishing may be carried out by dipping the tubular members into an electrolyte bath and passing a D.C. current through the bath with the tubular members being made the anode rather than the cathode as they would be in electroplating. In preferred embodiments electropolishing is carried out on the circumferential surfaces of the entire working length of at least one of the said inner and outer tubular member.

In the present invention, the significant improvements in the performance of the tubular surgical cutting instruments are brought about by applying the circumferential coating of a soft metal from the group consisting of silver and gold to the surface along at least a portion of the working length of at least one of the tubular members. The term "circumferential" is intended to mean the coating extends about substantially 360° around the portion of the tubular member to which it is applied so as to form a cylindrical wear resistant surface. Generally the portion along the working length to which the circumferential coating is applied may vary from the entire working length to just a short distance; e.g. about a quarter of of an inch which would provide a ring-like surface. As can be appreciated, when the coating of the metal from the group consisting of silver and gold is applied to only a short portion of the working length, the load bearing area will be relatively small and the use-life will be limited. Usually it is desirable that the coatings extend for at least about a half inch and preferably at least about an inch along the working length. In embodiments in which the coatings of the metal from the group silver and gold are applied to both tubular members, the coated portions may be adjacent to and coincide with one another when the tubular members are in an operational relationship; i.e. when the inner tubular member 24 is fully inserted in the outer tubular member 22, or they may be applied to different portions along the working lengths of the tubular members. In another useful embodiment of this invention, a silver coating may be applied to one of the tubular members and gold to the other member.

The silver and gold coatings used in the present invention usually comprise substantially about 100% of gold or silver, but when desired, they may comprise minor proportions of alloying materials which will not substantially adversely affect the malleability and softness of the coatings.

In experiments in which uncoated tubular surgical instruments were operated in air, it was observed that heat was mainly generated in the areas adjacent to the distal ends of the tubular members and it is in such areas that the coatings of the metal from the group consisting of silver and gold are most effective. Exceptionally good results were obtained using silver coatings. Accordingly, to this date, silver is the preferred coating material. Usually, in applying these coatings to the distal ends, the coatings 54 and 54a will distal ends to at least beyond the proximal ends 35 and 37 respectively of the cutting edges 34 and openings 36 as shown in FIGS. 2 and 3. More preferably, the coatings 54 and 54a will extend back from the ultimate distal end at least about an inch and one half.

Figures 4, 5, 6:
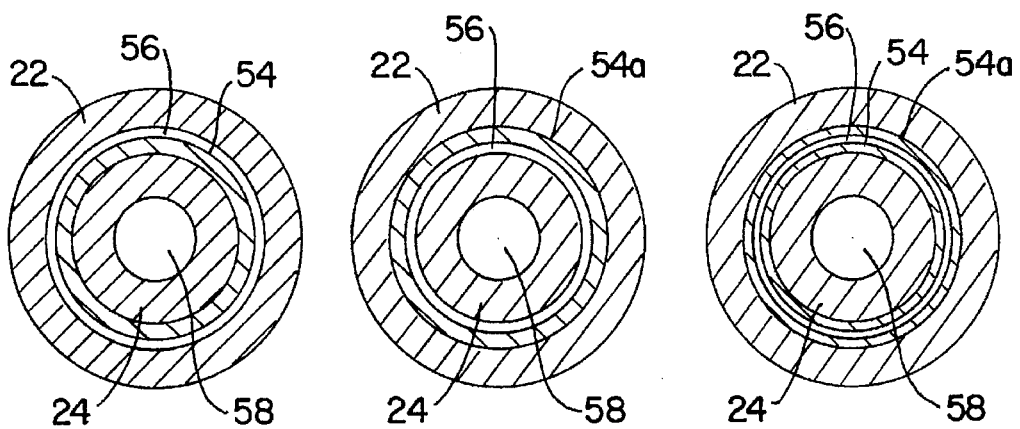
FIGS. 4, 5 and 6 are enlarged cross-sectional views along the line 2—2 of FIG. 2 illustrating three embodiments of tubular surgical instruments within the scope of the present invention.

In FIG. 4, FIG. 5 and FIG. 6, there are shown enlarged cross-sectional views along the line 2—2 of FIG. 2 showing various embodiments of the present invention in which the tolerance space 56 between the inner tubular member 24 and the outer tubular member 22 is exaggerated. In FIG. 4, there is shown an embodiment in which the coating of the metal from the group consisting of silver and gold 54 is applied only to the outer surface of the inner tubular member 24, in FIG. 5 an embodiment is shown in which the coating 54a is applied only to the inner surface of the outer tubular member 22, and in FIG. 6, there is shown an embodiment in which the coatings 54 and 54a are applied respectively to the outer surface of the inner tubular member 24 and the inner surface of the outer tubular member 22.

The silver and gold coatings of this invention are useful in designs of tubular surgical cutting instruments in which the outer tubular member is curved so as to permit it to gain access to areas which are difficult to reach and flexible tubing such as is used in plumber's augers (snakes) is used in making the inner tubular member.

In use, the tissue to be removed is exposed through the opening 36 in the outer tubular member 22 to the cutting edge 34 at the distal end 32 of the inner tubular member 24 which is rotated at high speeds by an electric motor (not shown). The severed tissue is removed by flushing the incision with a saline solution which in turn is removed along with the severed tissue th 58 in the inner tubular member 24 and out through lateral channel 48 into an aspiratory chamber (not shown) which is positioned around the shaf With the presence of the coatings of the metal from the group consisting of silver and gold, it has been found that the tubular surgical cutting instruments operate significantly smoother giving the surgeon greater control and the patient a safer procedure as the potential contamination of the tissue by metallic wear debris is virtually eliminated. This results in a level of performance never achievable before.

Having thus described the invention, what is claimed is:

1. A tubular surgical cutting instrument comprising:
   a) An inner tubular member having a proximal end and a distal end with a cutting edge disposed at said distal end;
   b) An outer tubular member having a proximal end and a distal end with an opening disposed at said distal end, the inner channel of said outer tubular member having a diameter sufficient to accommodate the rotation and positioning of said inner tubular member so that said cutting edge of said inner tubular member is adjacent to said opening in said outer tubular member to provide said cutting edge with access through said opening to the tissue to be severed; and
   c) A circumferential surface coating of a metal from the group consisting of silver and gold present along at least a portion of the working length of at least one of the outer surface of said inner tubular member and the inner surface of said outer tubular member whereby a wear resistant surface is provided to control and facilitate the rotation of said inner tubular member within said outer tubular member.

2. A cutting instrument as defined in claim 1 in which said circumferential surface coating of the metal from the group consisting of silver and gold is present along at least a portion of the working length of the outer surface of said inner tubular member.

3. A cutting instrument as defined in claim 1 in which said circumferential surface coating of metal from the group consisting of silver and gold is present along at least a portion of the working length of the inner surface of said outer tubular member.

4. A cutting instrument as defined in claim 1 in which said circumferential surface coating of a metal from the group consisting of silver and gold is present along at least a portion of the working length of both said outer surface of said inner tubular member and inner surface of said outer tubular member.

5. A cutting instrument as defined in claim 4 wherein said circumferential surface coating of metal from the group consisting of silver and gold on said inner tubular member is adjacent to said circumferential surface coating of the metal from the group consisting of silver and gold on said outer tubular member when said cutting edge of said inner tubular member is adjacent to said opening in said outer tubular member.

6. A cutting instrument as defined in claim 2 wherein said circumferential coating of the metal from the group consisting of silver and gold is present at the distal end of said inner tubular member and extends back from said distal end to at least beyond the proximal end of said cutting edge.

7. A cutting instrument as defined in claim 3 wherein said circumferential coating of the metal from the group consisting of silver and gold is present at the distal end of said outer tubular member and extends back from said distal end to at least beyond the proximal end of said opening.

8. A cutting instrument as defined in claim 5 wherein said circumferential surface coating of the metal from the group consisting of silver and gold on said inner tubular member is located at the distal end of said inner tubular member and extends back from said distal end to at least beyond the proximal end of said cutting edge and said circumferential surface coating of the metal from the group consisting of silver and gold on said outer tubular member is located at the distal end of said outer tubular member and extends back from said distal end to at least beyond the proximal end of said opening.

9. A cutting instrument as defined in claim 6 wherein said circumferential surface coating of the metal from the group consisting of silver and gold extends back at least one and one half inch from said distal end.

10. A cutting instrument as defined in claim 7 wherein said circumferential surface coating of the metal from the group consisting of silver and gold extends back at least one and one half inch from said distal end.

11. A cutting instrument as defined in claim 8 wherein said circumferential surface coating of the metal from the group consisting of silver and gold on said inner tubular member extends back at least one and one half inch from said distal end and said circumferential surface coating of the metal from the group consisting of silver and gold on said outer tubular member extends back at least about one and one half inch from said distal end.

12. A cutting instrument as defined in claim 1 wherein said circumferential surface coating of the metal from the group consisting of silver and gold is present over a subcoat selected from the group consisting of chromium, nickel, and carbides and nitrides of of zirconium, titanium, hafnium, tantalum, niobium, vanadium, tungsten, silicon and mixtures thereof.

13. A cutting instrument as defined in claim 1 wherein only one of said inner tubular member and said outer tubular member have present thereon a circumferential surface coating of the metal from the group consisting of silver and gold and the tubular member without said coating of the metal from the group consisting of silver and gold has present thereon along at least a portion of said working length a circumferential surface coating selected from the group consisting of chromium, nickel and carbides and nitrides of zirconium, titanium, hafnium, tantalum, niobium, vanadium, tungsten, silicon and mixtures thereof.

14. A cutting instrument as defined in claim 1 wherein the thickness of said circumferential surface coating of the metal from the group consisting of silver and gold is between about 60 Angstroms to about 50 microns.

15. A cutting instrument as defined in claim 1 in which the said circumferential coating of the metal from the group consisting of silver and gold extends for at least about one half inch along the working length of at least one of said outer surface of the inner tubular member and the said inner surface of the said outer tubular member.

16. A cutting instrument as defined in claim 1 in which the circumferential coating of the metal from the group consisting of silver and gold extends along about the entire working length of at least one of the said outer surface of the inner tubular member and the inner surface of the outer tubular member.

17. A tubular surgical instrument as defined in claim 1 in which said inner tubular member and said outer tubular member are formed from stainless steel and the circumferential surface along about the entire working length of at least one of said inner and said outer tubular members is electropolished.

18. A tubular surgical instrument as defined in claim 1 in which said outer tubular member is curved and said inner tubular member is formed from flexible tubing.

19. A tubular surgical cutting instrument as defined in claim 1, wherein said metal is silver.

* * * * *